United States Patent [19]
Slota et al.

[11] 3,937,071
[45] Feb. 10, 1976

[54] FATIGUE TEST APPARATUS

[75] Inventors: Stanley A. Slota, Sparta; Raymond F. Wegman, Ledgewood, both of N.J.

[73] Assignee: The United States of America as represented by the Secretary of the Army, Washington, D.C.

[22] Filed: July 11, 1975

[21] Appl. No.: 595,256

[52] U.S. Cl. ............................... 73/91; 73/95
[51] Int. Cl.² ............................... G01N 3/32
[58] Field of Search ...................... 73/91, 100, 95

[56] References Cited
UNITED STATES PATENTS

| | | | |
|---|---|---|---|
| 3,381,526 | 5/1968 | Rastugi et al. | 73/91 |
| 3,793,880 | 2/1974 | Sugi et al. | 73/91 X |

*Primary Examiner*—Jerry W. Myracle
*Attorney, Agent, or Firm*—Nathan Edelberg; Robert P. Gibson; Thomas R. Webb

[57] ABSTRACT

Four tensional test stations are mounted on a rectangular support frame made up of four channels. Each test station comprises an air cylinder attached to the frame and having a tensioning piston connected to a first specimen holder, a second specimen holder attached to the frame, a solenoid valve connected to each air cylinder, and a test terminate switch closed by the piston and first specimen holder. Current pulses are applied intermittently to each of the four stations by a motor-driven timer switch comprising a fixed contact plate, four spring contacts and a drive shaft having four shaped insulated cams engageable with the four spring contacts to move them into contact with the contact plate in a desired sequence. An electrical elapsed-time indicator is connected in parallel with the solenoid valve and timer switch contacts and in series with the test terminate switch, in each station. Compressed air is supplied from a source through a pressure regulator and a manifold to the inlets of the four solenoid valves. The support frame is partly enclosed by a box cover.

6 Claims, 5 Drawing Figures

FATIGUE TEST APPARATUS

BACKGROUND AND SUMMARY OF THE INVENTION

The present invention relates to a simple low-cost apparatus for low-rate tensional fatigue testing of multiple specimens. Most fatigue testing equipment available to date has been limited to heavy expensive indoor laboratory equipment that can test, at best, two specimens simultaneously.

In accordance with the invention, a single apparatus can be built to test a large number of specimens simultaneously at a low unit cost per test station, and in an outdoor environment. The new apparatus comprises: a rigid support frame; a plurality of test stations mounted on the frame; a source of air pressure and a manifold for conducting air from the source to the test stations; a voltage source; and a program timer switch comprising a plurality of switch contacts, one for each test station, and means for connecting one side of the voltage source to each of the contacts in a predetermined sequence. Each test station includes: a first specimen holder attached to the support frame; an air cylinder attached to the frame and having a piston to which a second specimen holder is attached; a solenoid valve having an air inlet connected to the manifold, an air outlet connected to the air cylinder and two electrical terminals; a single-pole-single-throw test terminate switch having two terminals and an actuating lever adapted to open the switch when the specimen fails, one of the switch terminals being connected to the other side of the voltage source, and the other switch terminal being connected to one terminal of the solenoid valve; and means connecting the other solenoid valve terminal to one of the contacts of the timer switch, to complete the circuit from the voltage source to the solenoid valve, whereby the failure of one specimen during testing interrupts the circuit of its station only. Preferably, an electrical elapsed-time indicator is connected in parallel with the solenoid valve and timer switch contacts and in series with the test terminate switch, in each station.

DETAILED DESCRIPTION OF A PREFERRED EMBODIMENT

Figure 1:
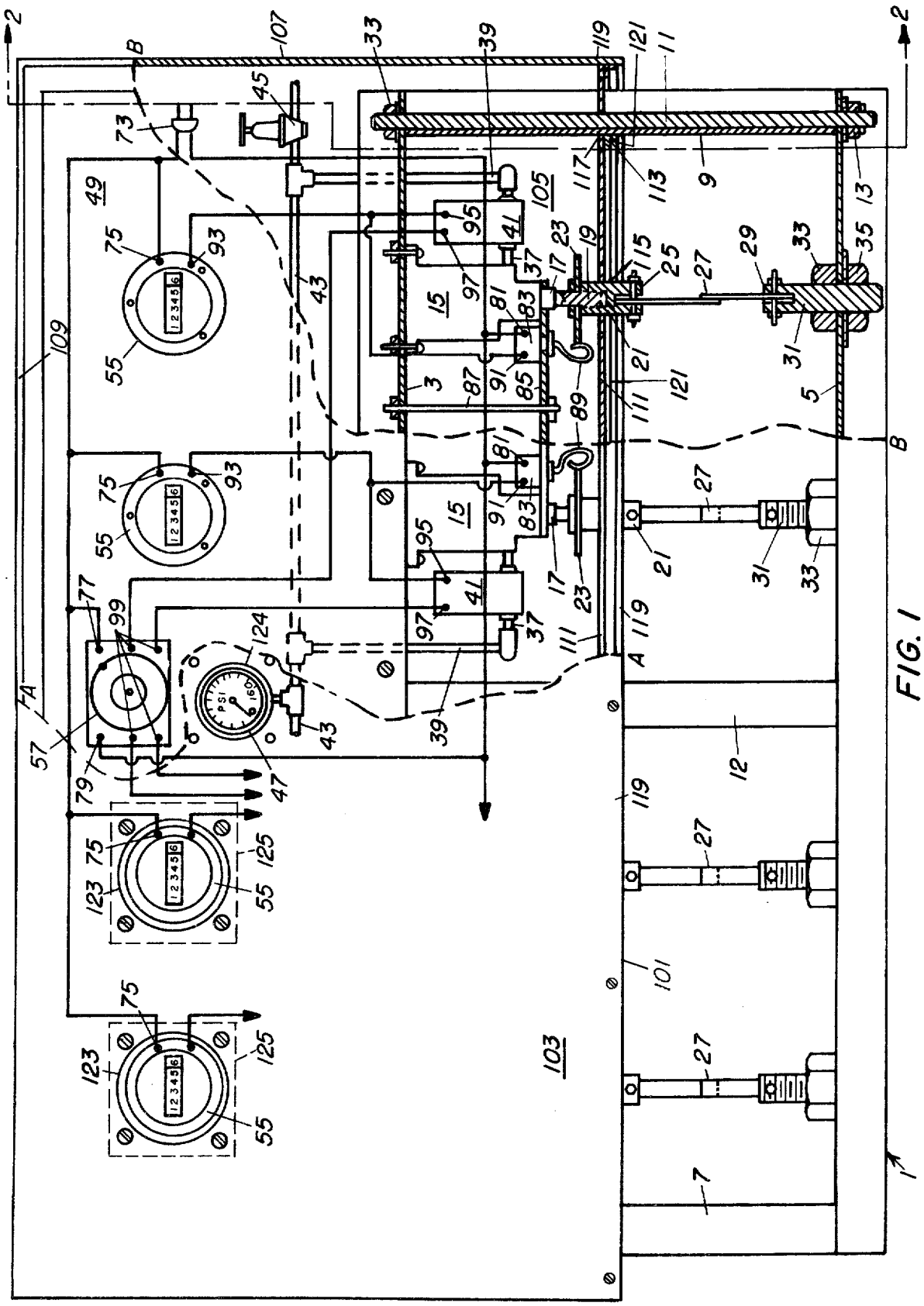
FIG. 1 is a side elevation, partly in section, of a fatigue test apparatus incorporating the present invention.
Figure 2:
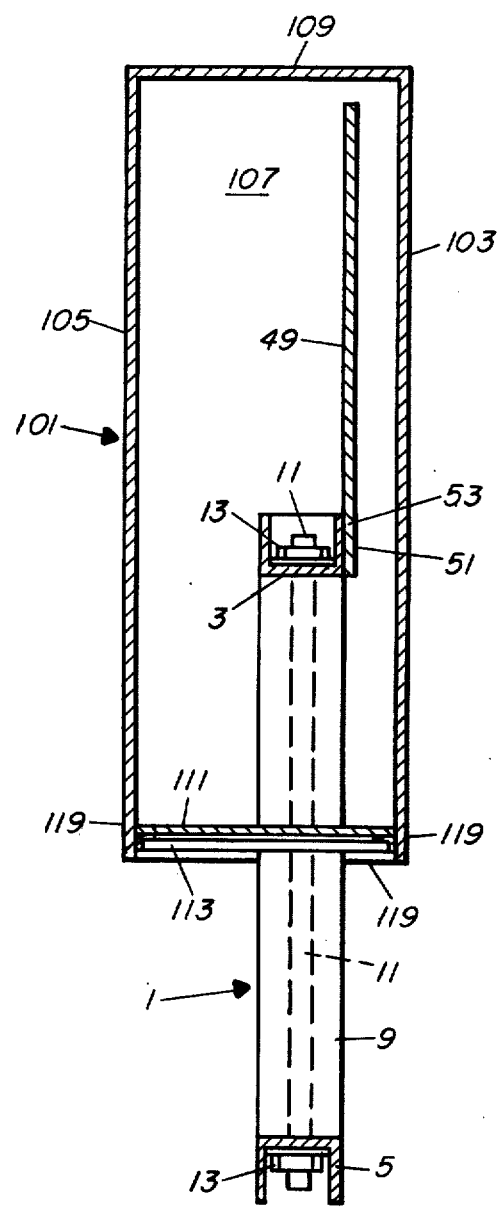
FIG. 2 is a vertical sectional view taken along line 2—2 of FIG. 1.

In the embodiment of the invention illustrated in FIGS. 1 and 2 of the drawing, the numeral 1 designates a rectangular frame made up of horizontal top and bottom channels 3 and 5 and vertical end channels 7 and 9, bolted together by two vertical bolts or studs 11 (one shown) with nuts 13. An intermediate bolted vertical channel 12 may also be provided. Four air cylinders 15 (two shown), mounted on the underside of the top channel 3, have pistons 17 with threaded ends 19 (one shown) extending downwardly therefrom. An upper specimen holder 21, threaded onto each piston end 19 has a switch actuating disc 23 attached to its upper end and a clevis or other means 25 for attaching the upper end of a specimen 27, such as a lap joint as shown, to the lower end of the holder. The lower end of the specimen 27 is attached to a clevis 29, for example, carried by a threaded lower holder 31 that is adjustably attached to the lower channel 5 of the frame 1, as by nuts 33 and 35. Each air cylinder 15 is connected, by piping 37 and 39 and a solenoid valve 41, to an air manifold 43. The manifold 43 is connected, through a pressure regulator 45, to an air source (not shown). A pressure gauge 47 may be connected to the manifold 43, to monitor the air pressure.

Figure 3:
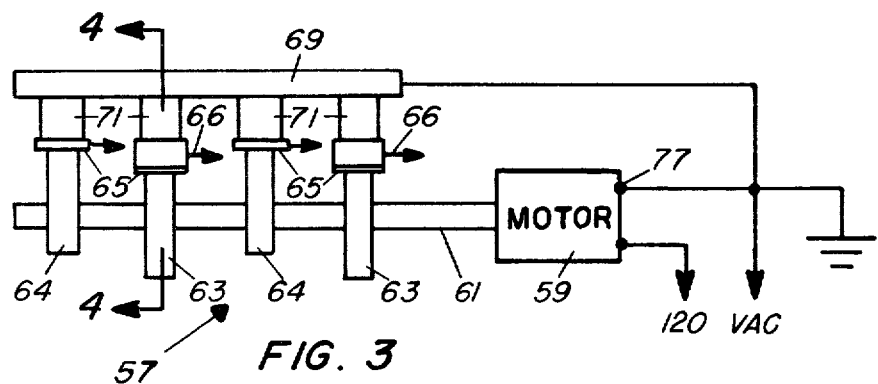
FIG. 3 is a partly schematic view of the timer switch.
Figure 4:
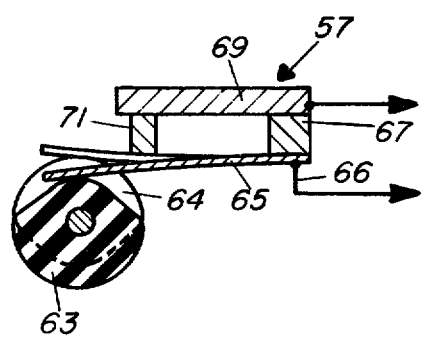
FIG. 4 is a transverse sectional view taken on line 4—4 of FIG. 3.

Most of the electrical equipment of the test apparatus is mounted on a rectangular support plate 49, attached at its lower edge to the front side of the upper channel 3, as shown best in FIG. 2. This electrical equipment comprises four electrical elapsed-time indicators 55, one for each test station, mounted on the front side of plate 49, and a program timer switch 57, mounted on the back side of plate 49. As shown in FIGS. 3 and 4, the switch 57 comprises a drive motor 59 having a rotary shaft 61 carrying four shaped insulating cams 63 and 64 that engage four leaf spring contacts 65, which are mounted by insulating posts 67 (one shown) on a conductive plate 69, and move the contacts 65 into contact with four fixed contacts 71 on the plate 69. Each contact 65 has a terminal 66. The cams 63 and 64 may be designed to actuate the contacts 65 in any desired sequence, such as in succession. The arrangement shown is designed to actuate the alternate test stations in pairs, to equalize the load on the test apparatus.

Figure 5:
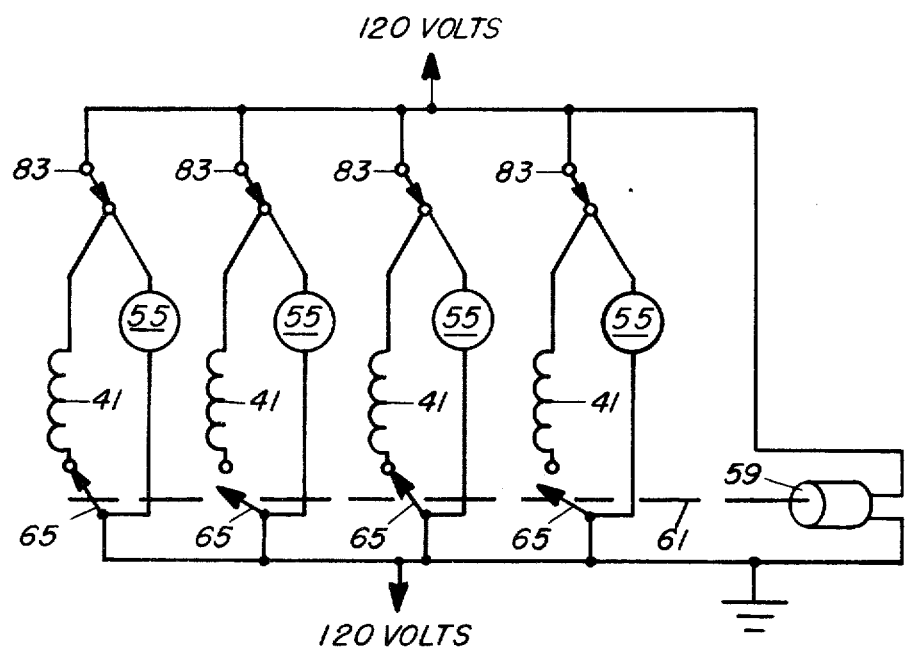
FIG. 5 is a circuit diagram of the apparatus of FIG. 1.

As shown in FIGS. 1, 3 and 5, one side (the upper one shown) of a voltage source plug 73 is connected to one terminal 75 of each time indicator 55 and also to one motor terminal 77 of timer switch 57. Terminal 77 is internally connected to switch plate 69. The other side of the plug 73 is connected to the other motor terminal 79 and also to one terminal 81 of each of four S.P.S.T. test terminate switches 83, one for each station, mounted on two plates 85 (one shown) suspended by rods or studs 87 from upper channel 3. Each test terminate switch 83 comprises a switch actuating lever 89 which engages disc 23 during assembly, to close the switch 83. A second terminal 91 of each switch 83 is connected to the other terminal 93 of the time indicator 55 of the same station and also to one terminal 95 of the solenoid valve 41 of the same station. The other terminal 97 of each solenoid valve 41 is connected to one of four terminals 99 of timer switch 57, which are connected respectively to the terminals 66 of the four switch contacts 65.

In operation, the four test specimens 27 are attached to the holders 21 and 31, and the nuts 33 and 35 are adjusted to take up the slack. In this assembly, the discs 23 actuate the levers 89 to close the switches 83. The manifold is pressurized by adjustment of valve 45, and the plug 73 is connected to a voltage source e.g. 120 volts AC. The switch motor 59 rotates the shaft 61 at uniform speed, and the cams 63 and 65 intermittently close and open the switches 65–71. As each switch 65–71 is closed, the electric current through that switch actuates the solenoid valve 41 connected therewith, which opens to apply air pressure from the manifold 43 to the associated air cylinder 15, resulting in upward movement of its piston 17 and tensioning of the test specimen connected thereto. As testing continues, each station is activated intermittently, thus subjecting each test specimen to repetitive fatigue. When any specimen fails in tension, the upper holder 21 moves upward disengaging disc 23 from lever 89, which interrupts the circuit in that station and stops the test without affecting the other stations. Each indicator 55 records the total time of testing at each station prior to opening of the test terminate switch thereof.

Preferably, the upper portion of the frame 1 is provided with a protective cover in the form of a rectangular box 101 made up of a front wall 103, a rear wall 105, end walls 107 (one shown), and top wall 109, attached together at their edges, as by welding. The box 101 is attached to the frame 1 by means of a bottom plate 111, which is attached to the end channels 7 and 9 by two angle pieces 113 (one shown). Plate 111 is formed with openings 115 and 117 to receive the holders 21 and end channels 7 and 9, respectively. The lower edges 119 of the walls 103 and 105 of box 101 are attached to plate 111 by means of angle pieces 121. In FIG. 1, the front plate 103 is cut away at broken line A—A, and the channels 3 and 5 and plates 49, 85 and 111 are partially cutaway at broken line B—B. The front plate 103 is provided with four circular openings 123 for viewing the time indicators 55, and a circular opening 124 for viewing the pressure gauge 47. Preferably, a transparent viewing plate 125 is mounted behind each opening 123 as shown in dotted lines in FIG. 1.

The foregoing disclosure and drawings are merely illustrative of the principles of this invention and are not to be interpreted in a limiting sense. We wish it to be understood that we do not desire to be limited to exact details of construction shown and described, because obvious modification will occur to a person skilled in the art.

What is claimed is:

1. Fatigue testing apparatus comprising: a rigid support frame, a plurality of test stations mounted on said support frame; a source of air pressure and a manifold for conducting air from said source to said stations; a voltage source; and a program timer switch comprising a plurality of switch contacts, one for each of said test stations, and means for connecting one side of said voltage source to each of said contacts in a predetermined sequence; each of said test stations including:

first and second spaced specimen holders adapted to be attached to opposite ends of a specimen to be tested, said first specimen holder being attached to said support frame;

an air cylinder attached to said support frame and having a piston to which said second specimen holder is attached;

a solenoid valve having an air inlet connected to said manifold, an air outlet connected to said air cylinder, and two electrical terminals;

a test terminate switch having two electrical terminals and an actuating lever engageable with an actuating member carried by said piston and second specimen holder and adapted to open the switch when the specimen fails, one of said terminal being connected to the other side of said voltage source, and the other terminal being connected to one terminal of said solenoid valve; and means connecting the other terminal of said solenoid valve to one of said plurality of switch contacts of said timer switch, to complete the circuit from said voltage source to said solenoid valve;

whereby the failure of one specimen during the testing of a plurality of specimens interrupts the voltage circuit of its station only.

2. An apparatus as in claim 1, wherein said timer switch means comprises a single switch contact connected to said one side of said voltage source and positioned adjacent to said plurality of switch contacts, and motor-driven cam means for moving each of said switch contacts into contact with said single switch contact in said sequence.

3. An apparatus as in claim 1, wherein each of said test stations further includes a voltage-responsive elapsed-time indicator connected between said one side of said voltage source and said other terminal of said test terminate switch for indicating the total time of test cycles for its test station only.

4. An apparatus as in claim 1, further comprising an air pressure regulator interposed between said air pressure source and said manifold.

5. An apparatus as in claim 4, further comprising an air pressure gauge connected to said manifold.

6. An apparatus as in claim 1, wherein there are an even number of test stations, and said timer switch is adapted to connect the voltage source to the odd and even stations alternately, to equalize the load on the support frame.

* * * * *